US00PP30860P2

(12) United States Plant Patent
Meilland

(10) Patent No.: US PP30,860 P2
(45) Date of Patent: Sep. 3, 2019

(54) HYBRID TEA ROSE PLANT NAMED 'MEITHATIE'

(50) Latin Name: *Rosa hybrida*
Varietal Denomination: MEITHATIE

(71) Applicant: THE CONARD-PYLE COMPANY, West Grove, PA (US)

(72) Inventor: Alain A. Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/932,661

(22) Filed: Apr. 5, 2018

(51) Int. Cl.
*A01H 5/02* (2018.01)
*A01H 6/74* (2018.01)

(52) U.S. Cl.
USPC ..... Plt./138
CPC ..... *A01H 6/74* (2018.05)

(58) Field of Classification Search
USPC ..... Plt./138, 139
CPC ..... A01H 5/0222
See application file for complete search history.

(56) References Cited

U.S. PATENT DOCUMENTS

PP11,836 P2 4/2001 Radler
2007/0011786 P1 1/2007 Meilland

*Primary Examiner* — Kent L Bell
(74) *Attorney, Agent, or Firm* — Buchanan Ingersoll & Rooney PC

(57) ABSTRACT

A new and distinct variety of Hybrid Tea Rose plant, herein referred to by its cultivar name, 'MEITHATIE', is provided which forms very abundantly on a nearly continuous basis attractive, cup-shaped, dark pink colored blossoms which emit a very pleasant strong fragrance. Attractive, glossy, very dense foliage is formed, which contrasts beautifully with the blossoms. The disease tolerance is very good, particularly against Black Spot and rust. The new variety is well suited for proving attractive ornamentation in the landscape and is very floriferous.

1 Drawing Sheet

Figures 1, 2, 3, 4, 5, 6, 7, 8, 9, 10, 11, 12, 13, 14, 15, 16:
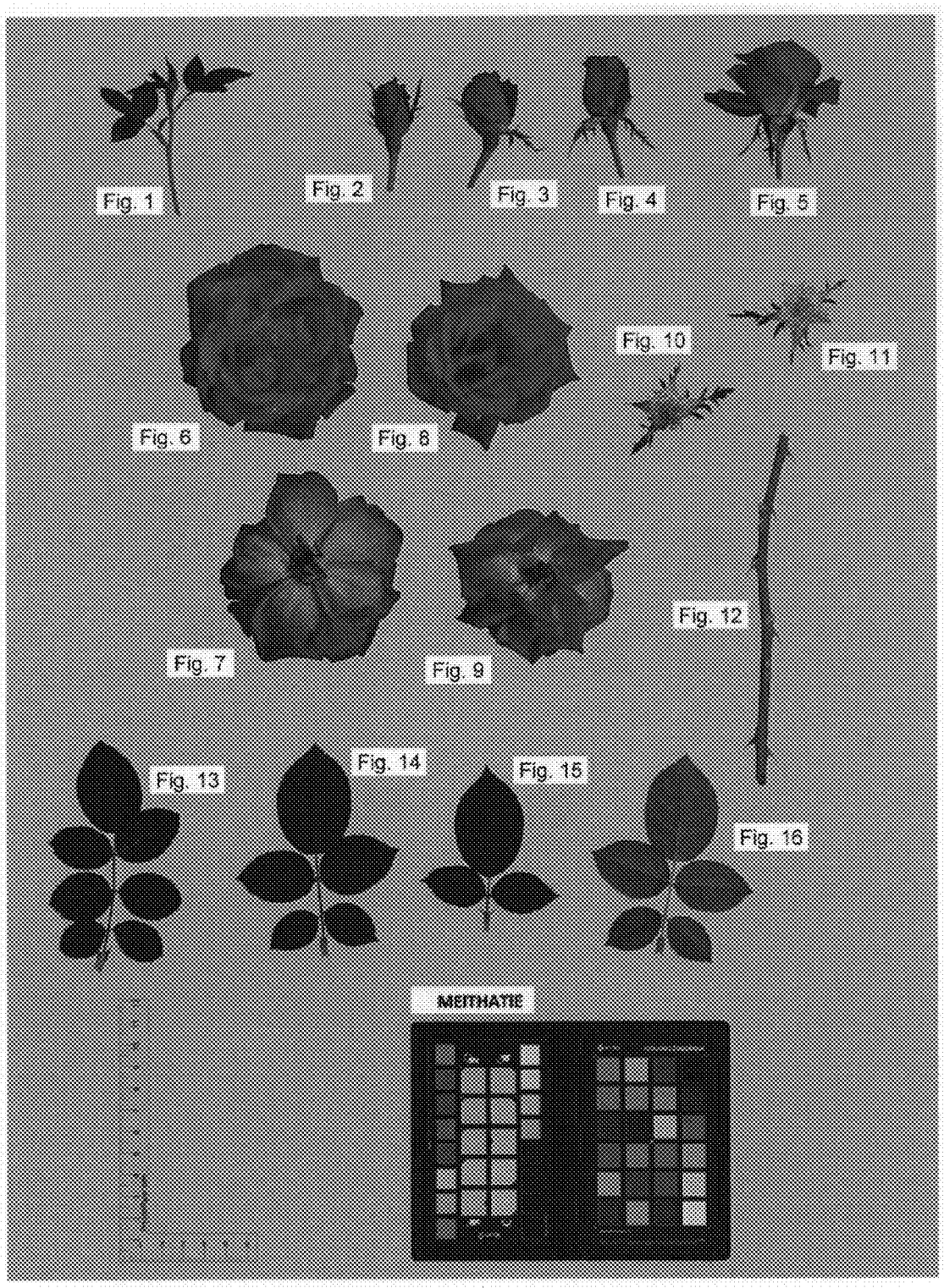

Botanical/commercial classification:
Latin name—*Rosa hybrida.*
Common name—Hybrid Tea Rose Plant.
Varietal denomination—'MEITHATIE'.

SUMMARY OF THE INVENTION

The new variety of *Rosa hybrida* Hybrid Tea Rose plant was created by artificial pollination wherein two parents were crossed which previously had been studied in the hope that they would contribute the desired characteristics. The female parent (i.e., the seed parent) was the 'MEIBDEROS' variety (U.S. Plant Patent Application Publication No. 2007/0011786, Abandoned). The male parent (i.e., the pollen parent) was the 'RADRAZZ' variety (U.S. Plant Pat. No. 11,836).

The parentage of the new variety can be summarized as follows:

'MEIBDEROS' x 'RADRAZZ'

The seeds resulting from the above pollination were sown and small plants were obtained which were physically and biologically different from each other. Selective study resulted in the identification of a single plant of the new variety.

It was found that the new variety of Hybrid Tea Rose plant of the present invention possesses the following combination of characteristics:

(a) very abundantly and nearly continuously forms attractive, cup-shaped, dark pink colored blossoms,
(b) forms attractive, very dense, glossy foliage, (c) exhibits very good tolerance to diseases, particularly against Black Spot and rust,
(d) is very floriferous,
(e) emits a very pleasant strong fragrance, and
(f) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEIBDEROS' variety (i.e., the seed parent) exhibits ocher to light pink colored blossoms, whereas the new variety exhibits darker pink colored blossoms. The 'RADRAZZ' variety (i.e., the pollen parent) displays single/semi-double-formed flowers possessing approximately 10 petals on average, while the new variety displays flowers possessing approximately 20-24 petals on average. Moreover, the new variety displays flowers which are larger in size than those displayed by the 'RADRAZZ' variety. Moreover, the new variety can be readily distinguished from other similar non-parental varieties. For example, the 'POULMAN' variety (U.S. Plant Pat. No. 6,264) exhibits a more upright plant habit and produces darker red colored flowers compared to the new variety.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'MEITHATIE'.

BRIEF DESCRIPTION OF THE PHOTOGRAPH

The accompanying photographs show as nearly true as it is reasonably possible to make the same, in a color illustration of this character, typical specimens of the plant parts of the new variety. The rose plants of the new variety were approximately two years of age and were observed during June while budded on their own roots and growing outdoors at Le Cannet des Maures, Var, France. Standard color information and dimensions in centimeters are included at the bottom of the photograph.

FIG. 1—illustrates a specimen of a young shoot.

FIG. 2—illustrates a specimen of a floral bud before the opening of the sepals.

FIG. 3—illustrates a specimen of a floral bud at the opening of the sepals.

FIG. 4—illustrates a specimen of a floral bud at the opening of the petals.

FIG. 5—illustrates a specimen of a flower in the course of opening.

FIG. 6—illustrates a specimen of a fully open flower—plan view—obverse.

FIG. 7—illustrates a specimen of a fully open flower—plan view—reverse.

FIG. 8—illustrates a specimen of a flower in the course of opening—plan view—obverse.

FIG. 9—illustrates a specimen of a flower in the course of opening—plan view—reverse.

FIG. 10—illustrates a specimen of a floral receptacle showing arrangement of the stamens and pistils.

FIG. 11—illustrates a specimen of a floral receptacle showing arrangement of the pistils (stamens removed).

FIG. 12—illustrates a specimen of a flowering stem.

FIG. 13—illustrates a specimen of a leaf with 7 leaflets—plan view—upper surface.

FIG. 14—illustrates a specimen of a leaf with 5 leaflets—plan view—upper surface.

FIG. 15—illustrates a specimen of a leaf with 3 leaflets—plan view—upper surface.

FIG. 16—illustrates a specimen of a leaf with 5 leaflets—plan view—under surface.

DETAILED BOTANICAL DESCRIPTION

The chart used in the identification of the colors is that of The Royal Horticultural Society (R.H.S. Color Chart), London, England. The terminology which precedes reference to the chart has been added to indicate the corresponding color in more common terms. The description is based on the observation of two-year-old specimens of the new variety during June while budded on their own roots and growing outdoors at Le Cannet des Maures, Var, France.

Class: Hybrid Tea Rose Plant.

Plant:

*Habit*.—Bushy.

*Height*.—Typically between 65 cm to 75 cm.

*Diameter*.—Approximately 75 cm on average.

Branches:

*Size*.—Length: typically between 30 cm to 50 cm. Diameter: typically between 0.4 cm to 0.8 cm.

*Color*.—Young stems: commonly near Yellow-Green Group 146D. Adult wood: commonly near Yellow-Green Group 146C.

*Thorns*.—Configuration on adult stems: slightly curved downward on the upper surface and concave on the under surface. Long prickles (≥0.7 cm) — quantity: commonly approximately 6 thorns per 10 cm long stem. Long prickles (≥0.7 cm) — base shape: oval. Long prickles (≥0.7 cm) — size: commonly near 0.7 cm in length on average. Long prickles (≥0.7 cm) — color: commonly near Yellow-Green Group 152C on young stems and commonly near Greyed-Orange Group 166B on adult stems. Small prickles (<0.7 cm) — none observed.

Foliage:

*General appearance*.—Very dense with a glossy aspect.

*Number of leaflets*.—3, 5, and 7; most often 5 or 7.

*Terminal leaflet*.—Length: approximately 8.0 cm on average. Width: approximately 5.7 cm on average.

*New foliage*.—Upper surface color: commonly near Yellow-Green Group 146B. Under surface color: commonly near Yellow-Green Group 147C.

*Adult foliage*.—Upper surface color: commonly near Yellow-Green Group 147A. Under surface color: commonly near Yellow-Green Group 148A.

*Entire leaf*.—Length: typically between 11.0 cm to 12.5 cm. Width: typically between 7.5 cm to 9.5 cm.

Leaflets:

*Shape*.—Tip: cuspidate. Base: obtuse.

*Texture*.—Leathery.

*General appearance*.—Oval.

*Edge*.—Slightly denticulate.

*Serration*.—Small and single.

*Petiole rachis*.—Length: typically between 3.0 cm to 4.5 cm. Diameter: typically between 0.1 cm to 0.2 cm. Color of upper surface: commonly near Yellow-Green Group 148B. Color of under surface: commonly near Yellow-Green Group 146C.

*Petioles*.—Upper surface: no glandular. Under surface: few prickles. Color of upper surface: commonly near Yellow-Green Group 147B to 147C. Color of under surface: commonly near Yellow-Green Group 148B. Length: typically between 2.5 cm to 3.5 cm. Petiole length of terminal leaflet: commonly near 3.0 cm on average. Petiole diameter of terminal leaflet: approximately 0.1 cm on average.

*Stipules*.—General appearance: adnate, pectinate and rather broad. Length: approximately 2.0 cm on average. Width: approximately 0.3 cm on average. Color of upper surface: commonly near Yellow-Green Group 146D. Color of under surface: commonly near Yellow-Green Group 146D.

Inflorescence:

*Number of flowers per stem*.—Generally between 1 and 5 flowers per stem.

*Lastingness of the bloom*.—Typically between 10 to 12 days.

*Bud*.—Shape: conical. Size: medium. Length: approximately 1.7 cm on average. Width: approximately 1.2 cm on average. Color as calyx breaks: Upper surface: commonly near Red Group 53A. Under surface: commonly near Red Group 53B to 53A.

*Sepals*.—Number: commonly 5. Length: approximately between 2.5 cm on average. Width: approximately near 0.7 cm on average. Shape: some, typically 0 to 7, narrow and elongated extensions (approximately near 2.0 to 3.0 cm on average), at the top: longish and narrow, at the base: upright. Upper surface: Texture: tomentous. Color: commonly near Yellow-Green Group 148D. Under surface: Texture: smooth. Color: commonly near Yellow-Green Group 148B.

*Receptacle*.—Color: commonly near Yellow-Green Group 148C. Length: approximately 0.8 cm on average. Width: approximately 0.6 cm on average. Surface: smooth. Shape: funnel shaped.

*Peduncle*.—Length: approximately near 4.3 cm on average. Width: approximately 0.2 cm on average. Surface: glandular. Color: commonly near Yellow-Green Group 148C.

*Flower*.—Average diameter when fully open: approximately 10 to 11 cm on average. Depth: typically 4.0 cm to 5.0 cm. Borne: commonly between 1 to 5 flowers per stem. Shape: cup shaped. Number of petals under normal conditions: approximately 20 to 24 petals on average. Shape of the petal: the base of the petal is obtuse with an undulated and round top. Texture of the petal: leathery. Petal length: approximately 3.4 cm on average. Petal width: approximately 3.2 cm on average. Petal arrangement: imbricated. Petal drop: petals drop off cleanly before drying. Fragrance: strong, fruity and rose tea fragrance. Color when opening: Upper surface: commonly near Red Group 53C suffused with near Red Group 53B; spot at the base is commonly near Yellow Group 7B. Under surface: commonly near Red-Purple Group 61B; spot at the base is commonly near Yellow Group 7B. Color of the open flower: Upper surface: commonly near Red-Purple Group 64C suffused with near Red-Purple Group 63A; spot at the base is commonly near Yellow Group 7B. Under surface: commonly near Red-Purple Group 64D to 64C; spot at the base is near Yellow Group 7B. Anthers: number is approximately 68 on average, length is approximately 0.2 cm on average, coloration is commonly near Yellow Group 8D, and arrangement is regular around styles. Filaments: length is approximately between 0.5 to 0.8 cm on average and coloration is commonly near Red Group 44B. Styles: length is approximately between 0.3 to 0.4 cm on average, the coloration is commonly near Red Group 44A, and the number is approximately 66 on average. Stigmas: size is approximately 0.1 cm on average and the coloration is commonly near Yellow Group 8D. Pollen: coloration is commonly near Yellow Group 8C. Hips: diameter is approximately 1.5 cm on average, shape is rounded, and coloration is commonly near Orange-Red Group 34C.

Development:

*Vegetation*.—Very strong.

*Blooming*.—Early in the season, typically May to November, very abundant and nearly continuous.

*Tolerance to disease*.—Very good, and particularly against Black Spot and rust.

The new 'MEITHATIE' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Hybrid Tea Rose plant characterized by the following combination of characteristics:

(a) very abundantly and nearly continuously forms attractive, cup-shaped, dark pink colored blossoms, (b) forms attractive, very dense, glossy foliage, (c) exhibits very good tolerance to diseases, particularly against Black Spot and rust, (d) is very floriferous, (e) emits a very pleasant strong fragrance, and (f) is well suited for providing attractive ornamentation; substantially as herein shown and described.

* * * * *

MEITHATIE